US012566185B2

(12) United States Patent　(10) Patent No.:　US 12,566,185 B2
Kawabe　(45) Date of Patent:　Mar. 3, 2026

(54) BLOOD COAGULATION TIME MEASUREMENT METHOD

(71) Applicant: SEKISUI MEDICAL CO., LTD., Chuo-ku (JP)

(72) Inventor: Toshiki Kawabe, Chuo-ku (JP)

(73) Assignee: SEKISUI MEDICAL CO., LTD., Chuo-ku (JP)

( * ) Notice: Subject to any disclaimer, the term of this patent is extended or adjusted under 35 U.S.C. 154(b) by 781 days.

(21) Appl. No.: 17/905,697

(22) PCT Filed: Mar. 5, 2021

(86) PCT No.: PCT/JP2021/008734
§ 371 (c)(1),
(2) Date: Sep. 6, 2022

(87) PCT Pub. No.: WO2021/177452
PCT Pub. Date: Sep. 10, 2021

(65) Prior Publication Data
US 2023/0152335 A1　May 18, 2023

(30) Foreign Application Priority Data
Mar. 6, 2020　(JP) ................................. 2020-039344

(51) Int. Cl.
*G01N 33/86*　(2006.01)
*G01N 33/49*　(2006.01)
*G01N 21/27*　(2006.01)
*G01N 21/82*　(2006.01)

(52) U.S. Cl.
CPC ......... *G01N 33/86* (2013.01); *G01N 33/4905* (2013.01); *G01N 21/272* (2013.01); *G01N 21/82* (2013.01); *G01N 2333/75* (2013.01)

(58) Field of Classification Search
CPC .. G01N 33/4905; G01N 33/86; G01N 21/272; G01N 21/82; G01N 2333/75
USPC ................................. 436/63, 69, 164; 422/73
See application file for complete search history.

(56) References Cited

U.S. PATENT DOCUMENTS

| | | | |
|---|---|---|---|
| 6,524,861 B1 | 2/2003 | Anderson | |
| 2018/0306820 A1* | 10/2018 | Suzuki | ............... G01N 33/4905 |
| 2021/0333295 A1 | 10/2021 | Kawabe et al. | |
| 2022/0146537 A1 | 5/2022 | Kawabe et al. | |
| 2023/0341371 A1* | 10/2023 | Kawabe | ................. G01N 33/86 |
| 2023/0341423 A1* | 10/2023 | Kawabe | ............. G01N 33/4905 |

FOREIGN PATENT DOCUMENTS

| | | |
|---|---|---|
| EP | 3 882 628 A1 | 9/2021 |
| EP | 3 919 913 A1 | 12/2021 |
| JP | 6-249855 A | 9/1994 |
| JP | 2019-86518 A | 6/2019 |
| WO | 2020/101025 A1 * | 5/2020 |

OTHER PUBLICATIONS

Extended European Search Report issued Dec. 11, 2023 in European Patent Application No. 21764679.3, 9 pages.
International Search Report mailed on May 18, 2021 in PCT/JP2021/008734 filed on Mar. 5, 2021 (3 pages).
Ogiwara, K. et al., "Development of a diagnostic algorithm for hemophilia A by template matching of the waveform in the APTT coagulation", Japanese Journal of Thrombosis and Hemostasis, 2019, vol. 30, No. 2, total 3 pages.
Wada, H., "APTT waveform", Japanese Journal of Thrombosis and Hemostasis, 2018, vol. 29 No.4, pp. 413-420, 9 total pages.

* cited by examiner

*Primary Examiner* — Maureen Wallenhorst
(74) *Attorney, Agent, or Firm* — Oblon, McClelland, Maier & Neustadt, L.L.P.

(57) ABSTRACT

Provided is a method for accurately measuring coagulation time of blood samples showing various coagulation reactions. The method for measuring blood coagulation time includes measuring coagulation reaction of a sample prepared by mixing a subject specimen and a coagulation time measurement reagent; calculating weighted average time of a calculation target area of a waveform related to coagulation velocity from the resulting measurement data; and determining the weighted average time as blood coagulation time.

7 Claims, 15 Drawing Sheets

| SAMPLE No. | CONTROL (sec) | 5% | 10% | 15% | 20% | 25% | 30% | 35% | 40% | 45% | 50% | 55% | 60% | 65% | 70% | 75% | 80% | 85% | 90% | 95% |
|---|---|---|---|---|---|---|---|---|---|---|---|---|---|---|---|---|---|---|---|---|
| 1 | 27.2 | | | | | | | | | | | | | | | | | | | |
| 2 | 28.6 | | | | | | | | | | | | | | | | | | | |
| 3 | 29.9 | | | | | | | | | | | | | | | | | | | |
| 4 | 30.9 | | | | | | | | | | | | | | | | | | | |
| 5 | 31.2 | | | | | | | | | | | | | | | | | | | |
| 6 | 31.3 | | | | | | | | | | | | | | | | | | | |
| 7 | 31.7 | | | | | | | | | | | | | | | | | | | |
| 8 | 32.1 | | | | | | | | | | | | | | | | | | | |
| 9 | 34.2 | | | | | | | | | | | | | | | | | | | |
| 10 | 35.1 | | | | | | | | | | | | | | | | | | | |
| 11 | 35.4 | | | | | | | | | | | | | | | | | | | |
| 12 | 38.2 | | | | | | | | | | | | | | | | | | | |
| 13 | 38.3 | | | | | | | | | | | | | | | | | | | |
| 14 | 42.3 | | | | | | | | | | | | | | | | | | | |
| 15 | 55.0 | | | | | | | | | | | | | | | | | | | |
| 16 | 60.5 | | | | | | | | | | | | | | | | | | | |
| 17 | 75.1 | | | | | | | | | | | | | | | | | | | |
| 18 | 77.9 | | | | | | | | | | | | | | | | | | | |
| 19 | 78.4 | | | | | | | | | | | | | | | | | | | |
| 20 | 81.0 | | | | | | | | | | | | | | | | | | | |
| 21 | 87.6 | | | | | | | | | | | | | | | | | | | |
| 22 | 119.1 | | | | | | | | | | | | | | | | | | | |
| 23 | 126.2 | | | | | | | | | | | | | | | | | | | |
| 24 | 141.2 | | | | | | | | | | | | | | | | | | | |

B

| SAMPLE No. | CONTROL (sec) | 5% | 10% | 15% | 20% | 25% | 30% | 35% | 40% | 45% | 50% | 55% | 60% | 65% | 70% | 75% | 80% | 85% | 90% | 95% |
|---|---|---|---|---|---|---|---|---|---|---|---|---|---|---|---|---|---|---|---|---|
| 1 | 27.2 | | | | | | | | | | | | | | | | | | | |
| 2 | 28.6 | | | | | | | | | | | | | | | | | | | |
| 3 | 29.9 | | | | | | | | | | | | | | | | | | | |
| 4 | 30.9 | | | | | | | | | | | | | | | | | | | |
| 5 | 31.2 | | | | | | | | | | | | | | | | | | | |
| 6 | 31.3 | | | | | | | | | | | | | | | | | | | |
| 7 | 31.7 | | | | | | | | | | | | | | | | | | | |
| 8 | 32.1 | | | | | | | | | | | | | | | | | | | |
| 9 | 34.2 | | | | | | | | | | | | | | | | | | | |
| 10 | 35.1 | | | | | | | | | | | | | | | | | | | |
| 11 | 35.4 | | | | | | | | | | | | | | | | | | | |
| 12 | 38.2 | | | | | | | | | | | | | | | | | | | |
| 13 | 38.3 | | | | | | | | | | | | | | | | | | | |
| 14 | 42.3 | | | | | | | | | | | | | | | | | | | |
| 15 | 55.0 | | | | | | | | | | | | | | | | | | | |
| 16 | 60.5 | | | | | | | | | | | | | | | | | | | |
| 17 | 75.1 | | | | | | | | | | | | | | | | | | | |
| 18 | 77.9 | | | | | | | | | | | | | | | | | | | |
| 19 | 78.4 | | | | | | | | | | | | | | | | | | | |
| 20 | 81.0 | | | | | | | | | | | | | | | | | | | |
| 21 | 87.6 | | | | | | | | | | | | | | | | | | | |
| 22 | 119.1 | | | | | | | | | | | | | | | | | | | |
| 23 | 126.2 | | | | | | | | | | | | | | | | | | | |
| 24 | 141.2 | | | | | | | | | | | | | | | | | | | |

| SAMPLE No. | CONTROL (sec) | 5% | 10% | 15% | 20% | 25% | 30% | 35% | 40% | 45% | 50% | 55% | 60% | 65% | 70% | 75% | 80% | 85% | 90% | 95% |
|---|---|---|---|---|---|---|---|---|---|---|---|---|---|---|---|---|---|---|---|---|
| 1 | 9.5 | | | | | | | | | | | | | | | | | | | |
| 2 | 11.4 | | | | | | | | | | | | | | | | | | | |
| 3 | 11.4 | | | | | | | | | | | | | | | | | | | |
| 4 | 11.4 | | | | | | | | | | | | | | | | | | | |
| 5 | 11.5 | | | | | | | | | | | | | | | | | | | |
| 6 | 11.6 | | | | | | | | | | | | | | | | | | | |
| 7 | 11.7 | | | | | | | | | | | | | | | | | | | |
| 8 | 11.8 | | | | | | | | | | | | | | | | | | | |
| 9 | 12.1 | | | | | | | | | | | | | | | | | | | |
| 10 | 12.1 | | | | | | | | | | | | | | | | | | | |
| 11 | 15.8 | | | | | | | | | | | | | | | | | | | |
| 12 | 17.0 | | | | | | | | | | | | | | | | | | | |
| 13 | 17.2 | | | | | | | | | | | | | | | | | | | |
| 14 | 20.6 | | | | | | | | | | | | | | | | | | | |
| 15 | 21.9 | | | | | | | | | | | | | | | | | | | |
| 16 | 23.4 | | | | | | | | | | | | | | | | | | | |
| 17 | 25.2 | | | | | | | | | | | | | | | | | | | |
| 18 | 25.6 | | | | | | | | | | | | | | | | | | | |
| 19 | 28.6 | | | | | | | | | | | | | | | | | | | |
| 20 | 31.3 | | | | | | | | | | | | | | | | | | | |
| 21 | 34.8 | | | | | | | | | | | | | | | | | | | |
| 22 | 43.0 | | | | | | | | | | | | | | | | | | | |
| 23 | 51.6 | | | | | | | | | | | | | | | | | | | |

B

| SAMPLE No. | CONTROL (sec) | 5% | 10% | 15% | 20% | 25% | 30% | 35% | 40% | 45% | 50% | 55% | 60% | 65% | 70% | 75% | 80% | 85% | 90% | 95% |
|---|---|---|---|---|---|---|---|---|---|---|---|---|---|---|---|---|---|---|---|---|
| 1 | 9.5 | | | | | | | | | | | | | | | | | | | |
| 2 | 11.4 | | | | | | | | | | | | | | | | | | | |
| 3 | 11.4 | | | | | | | | | | | | | | | | | | | |
| 4 | 11.4 | | | | | | | | | | | | | | | | | | | |
| 5 | 11.5 | | | | | | | | | | | | | | | | | | | |
| 6 | 11.6 | | | | | | | | | | | | | | | | | | | |
| 7 | 11.7 | | | | | | | | | | | | | | | | | | | |
| 8 | 11.8 | | | | | | | | | | | | | | | | | | | |
| 9 | 12.1 | | | | | | | | | | | | | | | | | | | |
| 10 | 12.1 | | | | | | | | | | | | | | | | | | | |
| 11 | 15.8 | | | | | | | | | | | | | | | | | | | |
| 12 | 17.0 | | | | | | | | | | | | | | | | | | | |
| 13 | 17.2 | | | | | | | | | | | | | | | | | | | |
| 14 | 20.6 | | | | | | | | | | | | | | | | | | | |
| 15 | 21.9 | | | | | | | | | | | | | | | | | | | |
| 16 | 23.4 | | | | | | | | | | | | | | | | | | | |
| 17 | 25.2 | | | | | | | | | | | | | | | | | | | |
| 18 | 25.6 | | | | | | | | | | | | | | | | | | | |
| 19 | 28.6 | | | | | | | | | | | | | | | | | | | |
| 20 | 31.3 | | | | | | | | | | | | | | | | | | | |
| 21 | 34.8 | | | | | | | | | | | | | | | | | | | |
| 22 | 43.0 | | | | | | | | | | | | | | | | | | | |
| 23 | 51.6 | | | | | | | | | | | | | | | | | | | |

| SAMPLE No. | CONCENTRATION (mg/dL) | 5% | 10% | 15% | 20% | 25% | 30% | 35% | 40% | 45% | 50% | 55% | 60% | 65% | 70% | 75% | 80% | 85% | 90% | 95% |
|---|---|---|---|---|---|---|---|---|---|---|---|---|---|---|---|---|---|---|---|---|
| 1 | 98 | | | | | | | | | | | | | | | | | | | |
| 2 | 98 | | | | | | | | | | | | | | | | | | | |
| 3 | 196 | | | | | | | | | | | | | | | | | | | |
| 4 | 196 | | | | | | | | | | | | | | | | | | | |
| 5 | 294 | | | | | | | | | | | | | | | | | | | |
| 6 | 294 | | | | | | | | | | | | | | | | | | | |
| 7 | 392 | | | | | | | | | | | | | | | | | | | |
| 8 | 392 | | | | | | | | | | | | | | | | | | | |
| 9 | 490 | | | | | | | | | | | | | | | | | | | |
| 10 | 490 | | | | | | | | | | | | | | | | | | | |
| 11 | 588 | | | | | | | | | | | | | | | | | | | |
| 12 | 588 | | | | | | | | | | | | | | | | | | | |
| 13 | 686 | | | | | | | | | | | | | | | | | | | |
| 14 | 686 | | | | | | | | | | | | | | | | | | | |
| 15 | 784 | | | | | | | | | | | | | | | | | | | |
| 16 | 784 | | | | | | | | | | | | | | | | | | | |
| 17 | 882 | | | | | | | | | | | | | | | | | | | |
| 18 | 882 | | | | | | | | | | | | | | | | | | | |
| 19 | 980 | | | | | | | | | | | | | | | | | | | |
| 20 | 980 | | | | | | | | | | | | | | | | | | | |

B

| SAMPLE No. | CONCENTRATION (mg/dL) | 5% | 10% | 15% | 20% | 25% | 30% | 35% | 40% | 45% | 50% | 55% | 60% | 65% | 70% | 75% | 80% | 85% | 90% | 95% |
|---|---|---|---|---|---|---|---|---|---|---|---|---|---|---|---|---|---|---|---|---|
| 1 | 98 | | | | | | | | | | | | | | | | | | | |
| 2 | 98 | | | | | | | | | | | | | | | | | | | |
| 3 | 196 | | | | | | | | | | | | | | | | | | | |
| 4 | 196 | | | | | | | | | | | | | | | | | | | |
| 5 | 294 | | | | | | | | | | | | | | | | | | | |
| 6 | 294 | | | | | | | | | | | | | | | | | | | |
| 7 | 392 | | | | | | | | | | | | | | | | | | | |
| 8 | 392 | | | | | | | | | | | | | | | | | | | |
| 9 | 490 | | | | | | | | | | | | | | | | | | | |
| 10 | 490 | | | | | | | | | | | | | | | | | | | |
| 11 | 588 | | | | | | | | | | | | | | | | | | | |
| 12 | 588 | | | | | | | | | | | | | | | | | | | |
| 13 | 686 | | | | | | | | | | | | | | | | | | | |
| 14 | 686 | | | | | | | | | | | | | | | | | | | |
| 15 | 784 | | | | | | | | | | | | | | | | | | | |
| 16 | 784 | | | | | | | | | | | | | | | | | | | |
| 17 | 882 | | | | | | | | | | | | | | | | | | | |
| 18 | 882 | | | | | | | | | | | | | | | | | | | |
| 19 | 980 | | | | | | | | | | | | | | | | | | | |
| 20 | 980 | | | | | | | | | | | | | | | | | | | |

BLOOD COAGULATION TIME MEASUREMENT METHOD

This application is a national stage application of PCT/JP2021/008734, filed Mar. 5, 2021, which claims priority to Japanese application 2020-039344, filed Mar. 6, 2020, the contents of both applications are incorporated herein by reference.

FIELD OF THE INVENTION

The present invention relates to a method for measuring blood coagulation time.

BACKGROUND OF THE INVENTION

A blood coagulation test is a test for diagnosing blood coagulability of a patient by adding a prescribed reagent to a blood sample of the patient and measuring, for example, the blood coagulation time. Typical examples of the blood coagulation time include prothrombin time (PT), activated partial thromboplastin time (APTT), and thrombin time. The blood coagulation test can examine the hemostatic ability and fibrinolytic capacity of a patient. An abnormality in the blood coagulation ability mainly causes elongation of the coagulation time. For example, elongation of coagulation time is caused by, for example, effect of an anticoagulant, reduction of a coagulation-participating component, congenital deficiency of a blood coagulation factor, and an acquired autoantibody that inhibits coagulation reaction.

In recent years, automated analyzers that perform automatic measurement for blood coagulation tests are being widely used, and blood coagulation tests can be easily carried out. For example, in some kind of automated analyzer, a mixed solution obtained by adding a reagent to a blood sample is illuminated with light, and the coagulation reaction of the blood sample is measured based on the resulting change in the amount of light. For example, when the amount of scattered light is measured, the scattered light intensity is sharply increased, by progression of coagulation, at a point of time after a certain amount of time has passed since the addition of the reagent to a blood sample, then saturates as the coagulation reaction approaches the end, and reaches the plateau. The blood coagulation time can be measured based on such a temporal change in scattered light intensity.

As the method for calculating coagulation time by an automated analyzer, several procedures, such as a percentage method and a differentiation method, are used (see Patent Literature 1). When the coagulation time is calculated based on the amount of scattered light, in a percentage method, typically, the time until the measured scattered light intensity reaches a certain percentage of the maximum value thereof is calculated as the coagulation time. The percentage method can quite accurately calculate the coagulation time not only of a normal sample but also of an abnormal sample, such as a low-fibrinogen sample, a chyle sample, and a hemolyzed blood sample. However, the automatic analysis based on the percentage method needs to set the sample measurement time long such that the maximum amount of scattered light can be detected even in an abnormal sample with low coagulability, such as a low-fibrinogen sample. Therefore, the analysis takes time.

In a differentiation method, typically, the time until the differential value of the amount of scattered light reaches the peak or a certain percentage thereof is calculated as the coagulation time. However, in the abnormal sample with low coagulability, such as a low-fibrinogen sample, no clear peak of the differential value of the amount of scattered light is observed in some cases. In addition, in the abnormal sample, two or more peaks of the differential value are observed in some cases. A procedure of calculating the coagulation time based on a single-peak curve formed by fitting of a differential value curve may be used, the fitting impairs the accurate information relating to the coagulability of a sample in some cases.

Furthermore, photometric data from an analyzer include various noises caused by the apparatus, the reagent, and the condition of the sample, and the noises may produce false detection of the coagulation time. The automatic analysis of a blood sample is required to calculate reliable coagulation time by removing the bad influence of noises.

CITATION LIST

Patent Literature

Patent Literature 1: JP-A-6-249855

SUMMARY OF THE INVENTION

Technical Problem

The present invention relates to a method for measuring blood coagulation time that can accurately measure coagulation time of blood samples showing various blood coagulation reaction curves.

Solution to Problem

That is, the present invention provides the followings:
[1] A method for measuring blood coagulation time, comprising:
  measuring coagulation reaction of a sample prepared by mixing a subject specimen and a coagulation time measurement reagent;
  calculating weighted average time of a calculation target area of a waveform related to coagulation velocity from the resulting measurement data; and
  determining blood coagulation time of the subject specimen based on the weighted average time, wherein
  the calculation target area is a region on or above a predetermined lower limit value of the waveform related to the coagulation velocity.
[2] The method according to [1], wherein the waveform related to coagulation velocity is a first-order differential curve of a coagulation reaction curve or its relative values.
[3] The method according to [1] or [2], wherein the weighted average time is represented by a following equation, where F(t) (t is time) is the waveform related to coagulation velocity, and t1 and t2 (t1 < t2) are times when F(t) is x % (x is a prescribed value set within a range of 5 to 95) of the maximum value of F(t):

$$\text{Weighted average time} = \frac{\sum_{i=t1}^{t2} (i \times F(i))}{\sum_{i=t1}^{t2} F(i)}.$$

[4] The method according to any one of [1] to [3], wherein the subject specimen is plasma.

[5] The method according to any one of [1] to [4], wherein the blood coagulation time is activated partial thromboplastin time (APTT), prothrombin time (PT), or coagulation time, of fibrinogen concentration measurement.

[6] A method for measuring coagulation factor concentration, comprising measuring coagulation factor concentration of a subject specimen based on blood coagulation time of the subject specimen measured by the method according to any one of the [1] to [5].

[7] The method according to [6], wherein the subject specimen is plasma.

[8] The method according to [6] or [7], wherein the coagulation factor is fibrinogen.

[9] The method according to [8], wherein the blood coagulation time is coagulation time by fibrinogen concentration measurement.

Advantageous Effects of the Invention

According to the method of the present invention, coagulation times of blood samples showing various blood coagulation reaction curves including a normal sample and an abnormal sample can be accurately measured. In addition, when a large number of samples are analyzed at real time with an automated analyzer, the method of the present invention can shorten the analysis time for one sample and can improve the analysis efficiency, compared to a conventional percentage method.

BRIEF DESCRIPTION OF DRAWINGS

FIG. 12 shows errors in weighted average time (vT5% to vT95%) in 5% to 95% calculation target areas of 24 samples with respect to a control (APTT by a percentage method). In the tables, the cells indicated by gray color indicate that the difference between the weighted average time and the control is within ±5% (A) or ±2.5% (B) of the control.

FIG. 15 shows errors in weighted average time (vT5% to vT95%) in 5% to 95% calculation target areas of 23 samples with respect to a control (PT by a percentage method). In the tables, the cells indicated by gray color indicate that the difference between the weighted average time and the control is within ±5% (A) or ±2.5% (B) of the control.

FIG. 18 shows errors in [Fbg] arithmetic values regarding concentration series sample data of 20 samples in 5% to 95% calculation target areas with respect to expected values. In the tables, the cells indicated by gray color indicate that the error of the arithmetic value from the expected value is within ±10% (A) or within ±5% (B).

DETAILED DESCRIPTION OF THE INVENTION

Figure 1:
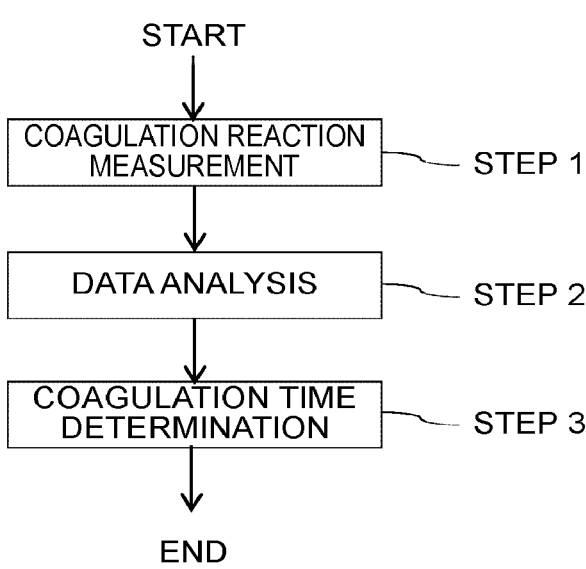
FIG. 1 is a basic flow chart of an embodiment of a method for measuring blood coagulation time of the present invention.

In a blood coagulation test, a prescribed reagent is added to a blood sample, a subsequent blood coagulation reaction is measured, and blood coagulation time is measured from the coagulation reaction. In the present specification below, a blood sample may be referred to as a sample. As the measurement of a blood coagulation reaction, a general method, for example, an optical method that measures the scattered light intensity, transmittance, absorbance, or the like, or a mechanical method that measures the viscosity of plasma is used. The coagulation reaction curve of a normal sample depends on the measurement method, but basically shows a sigmoid shape. For example, a coagulation reaction curve based on the scattered light intensity of a normal sample is usually sharply increased by progression of coagulation at a point of time when a certain amount of time has passed since the addition of the reagent, and then reaches the plateau as the coagulation reaction approaches the end. In contrast, the coagulation reaction curves of abnormal samples with coagulation disorder show various shapes depending on the cause of the abnormality, such as delay of the curve rise time and a gradual increase. The variety in the coagulation reaction curve of an abnormal sample makes accurate measurement of coagulation time in an automated analyzer difficult.

In conventional general measurement of blood coagulation time, data at least until the end of coagulation reaction are acquired, and the coagulation time is calculated based on the acquired data. For example, in the case of calculating coagulation time based on the amount of scattered light, there are, for example, a procedure of judging a point of time at which the scattered light intensity is saturated as the end of coagulation reaction, and then determining a point of time at which the coagulation reaction curve reaches the maximum velocity or 1/N thereof during from the time of addition of the reagent until the time of the end of coagulation reaction as the coagulation time (a differentiation method), and a procedure of determining a point of time at which the scattered light intensity reaches 1/N of the amount of scattered light at the end of coagulation reaction as the coagulation time (a percentage method, see Patent Literature 1). However, false detection of the peak of a coagulation reaction velocity or the end of coagulation reaction is caused by abnormal shapes and noises of coagulation reaction curves of abnormal samples as described above, and, for example, the peak of a reaction velocity and the reaction end are detected at a too early point of time in some cases. Such false detection leads to calculation of inaccurate coagulation time.

Since an automated analyzer efficiently analyzes a large number of samples, it is desirable to promptly end the measurement after acquisition of necessary data of one sample and to start measurement of a next sample. However, such a procedure has a risk of inviting the end of measurement too early due to the above-described false detection of the end of coagulation reaction at a too early point of time and causing missing of necessary data. On the other hand, if the coagulation reaction measurement time for one sample is fixed as a sufficiently long time, it is possible to prevent data missing due to false detection of the end of coagulation reaction. However, such a procedure makes the measurement time of a large number of samples unnecessarily long and thereby reduces the total analysis efficiency.

The present invention can prevent false detection of the coagulation time resulting from the abnormal shape of a coagulation reaction curve as described above to allow accurate coagulation time measurement. In addition, according to the present invention, since minimum necessary coagulation reaction measurement time can be applied to individual coagulation time measurements of various blood samples including a normal sample and an abnormal sample, the analysis time for one sample can be shortened.

[Method for Measuring Blood Coagulation Time]

The present invention relates to a method for measuring the blood coagulation time of a blood sample. The method for measuring blood coagulation time of the present invention (hereinafter, also referred to as the method of the present invention) includes measuring coagulation reaction of a sample prepared by mixing a subject specimen and a coagulation time measurement reagent and calculating weighted average time of a prescribed calculation target area of a waveform related to coagulation velocity from the resulting measurement data. An embodiment of the method of the present invention will be described with reference to FIG. 1. In the present method, first, a sample is prepared from a subject specimen, and coagulation reaction of the sample is then measured (step 1). The resulting measurement data are analyzed to acquire a waveform related to the coagulation velocity of the sample, and weighted average time of the prescribed calculation target area of the waveform is calculated (step 2). Based on the resulting weighted average time, the coagulation time of the subject specimen is determined (step 3).

1. Measurement of Coagulation Reaction

The measurement of coagulation reaction measures the coagulation reaction of a subject specimen mixed with a reagent. The blood coagulation time is measured from the data in the time series of the coagulation reaction obtained by this measurement. Examples of the blood coagulation time to be measured by the method of the present invention include prothrombin time (PT), activated partial thromboplastin time (APTT), and coagulation time in fibrinogen concentration (Fbg) measurement. In the present specification below, the method of the present invention will be mainly described using activated partial thromboplastin time (APTT) as an example of the coagulation time. The method of the present invention can be changed to another coagulation time (for example, prothrombin time (PT)) by those skilled in the art.

In the method of the present invention, as the blood subject specimen, plasma of a subject is preferably used. An anticoagulant that is usually used in a coagulation test may be added to the sample. For example, plasma is obtained by sampling blood with a blood collection tube containing sodium citrate and then performing centrifugation.

A coagulation time measurement reagent is added to the subject specimen to start blood coagulation reaction. The coagulation reaction of the mixed solution prepared by addition of the reagent can be measured. The coagulation time measurement reagent to be used can be arbitrarily selected depending on the measurement purpose. The reagents for measuring various types of coagulation time are commercially available (for example, APTT reagent Coagpia APTT-N, manufactured by Sekisui Medical Co., Ltd.). As the measurement of coagulation reaction, a general method, for example, an optical method that measures the amount of scattered light, transmittance, absorbance, or the like, or a mechanical method that measures the viscosity of plasma may be used. The point of time of starting coagulation reaction can be typically defined as the point of time at which the coagulation reaction is started by adding a reagent to a sample, but another timing may be defined as the point of time of starting the reaction. The time for continuing the measurement of coagulation reaction may be, for example, from several tens of seconds to about 7 minutes since the point of time of mixing a sample and a reagent. This measurement time may be an arbitrarily determined fixed value or may be until the point of time at which the end of coagulation reaction of each sample is detected. During the measurement time, measurement of the state of progress of the coagulation reaction (in the case of optical detection, photometry) is repeated at predetermined intervals. For example, measurement may be performed at 0.1 second intervals. The temperature of the mixed solution during the measurement is, for example, 30° C. or more and 40° C. or less under normal conditions, preferably 35° C. or more and 39° C. or less. Various conditions of measurement can be appropriately set depending on the subject specimen, reagent, measurement methods, and so on.

A series of procedure in the above-described measurement of coagulation reaction can be performed using an automated analyzer. An example of the automated analyzer is automated blood coagulation analyzer CP3000 (manufactured by Sekisui Medical Co., Ltd.). Alternatively, the procedure may be partially manually performed. For example, preparation of subject specimens is performed by a human, and the subsequent procedure can be performed with an automated analyzer.

2. Data Analysis 2.1) Pre-Processing of Data and Correction Processing

Figure 2:
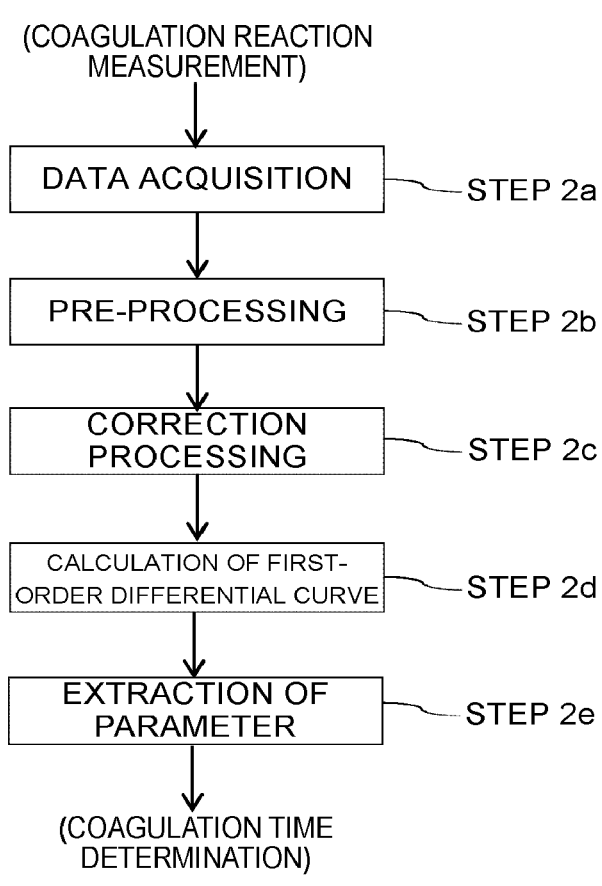
FIG. 2 is an embodiment of a process of a data analysis step shown in FIG. 1.

Subsequently, data analysis of step 2 will be described. The flow of data analysis is shown in FIG. 2. The data analysis of step 2 may be performed in parallel to the coagulation reaction measurement of step 1 or may be performed later using previously measured data of coagulation reaction measurement. Preferably, the data analysis of step 2 is performed in parallel to coagulation reaction measurement of step 1, coagulation reaction measurement of the sample is ended at the time when data necessary for calculation of coagulation time of the subject specimen are acquired, and the coagulation reaction measurement is transferred to a next sample.

In step 2a, the measurement data by coagulation reaction measurement are acquired. The data are, for example, data reflecting the coagulation reaction process of the sample obtained by APTT measurement in the above-described step 2. For example, obtained are data showing a change with time in the amount of progress of coagulation reaction (for example, scattered light intensity) of a sample containing a subject specimen and a coagulation time measurement reagent after addition of a calcium chloride solution. These data obtained by the coagulation reaction measurement are also referred to as coagulation reaction information in the present specification.

Figure 3:
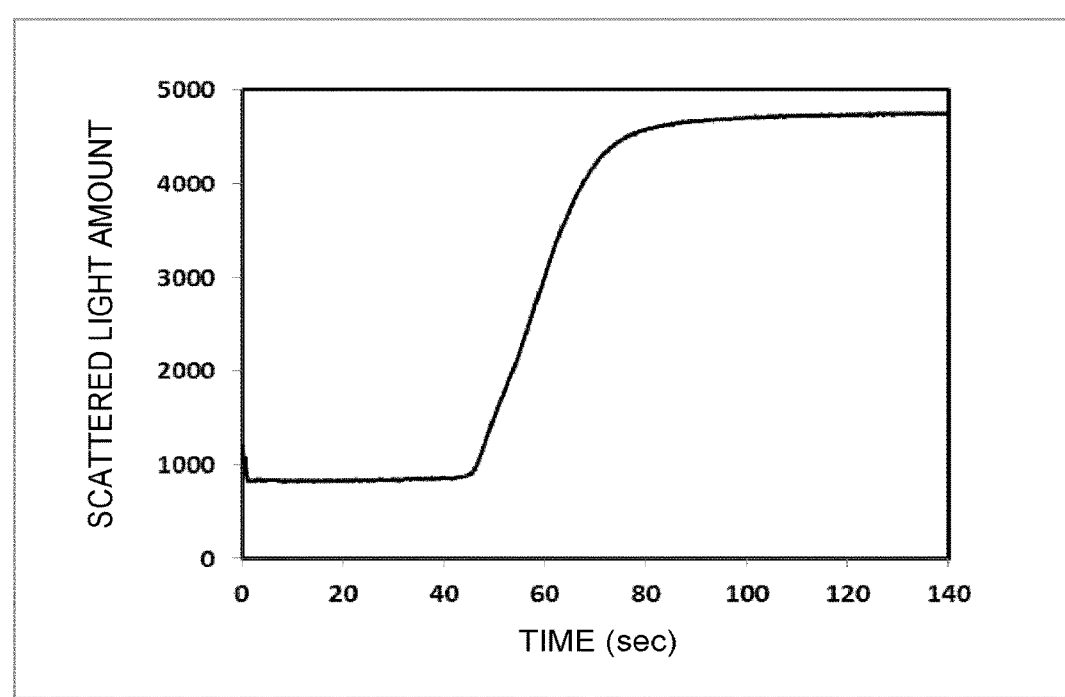
FIG. 3 is an example of a coagulation reaction curve.

FIG. 3 shows an example of coagulation reaction information acquired in step 2a. FIG. 3 is a coagulation reaction curve based on the amount of scattered light, where the horizontal axis represents the time (coagulation reaction time) passed after addition of the calcium chloride solution, and the vertical axis represents the amount of scattered light. Since the coagulation reaction of the mixed solution progresses, the scattered light intensity increases with time. In the present specification, such a curve showing the change in the amount of coagulation reaction with respect to the time of the coagulation reaction is referred to as a coagulation reaction curve.

A coagulation reaction curve based on the amount of scattered light as shown in FIG. 3 is usually sigmoid-like. On the other hand, a coagulation reaction curve based on the amount of transmitted light is usually inverse sigmoid-like. In the present specification below, data analysis using a coagulation reaction curve based on the amount of scattered light as coagulation reaction information will be described.

Figure 4:
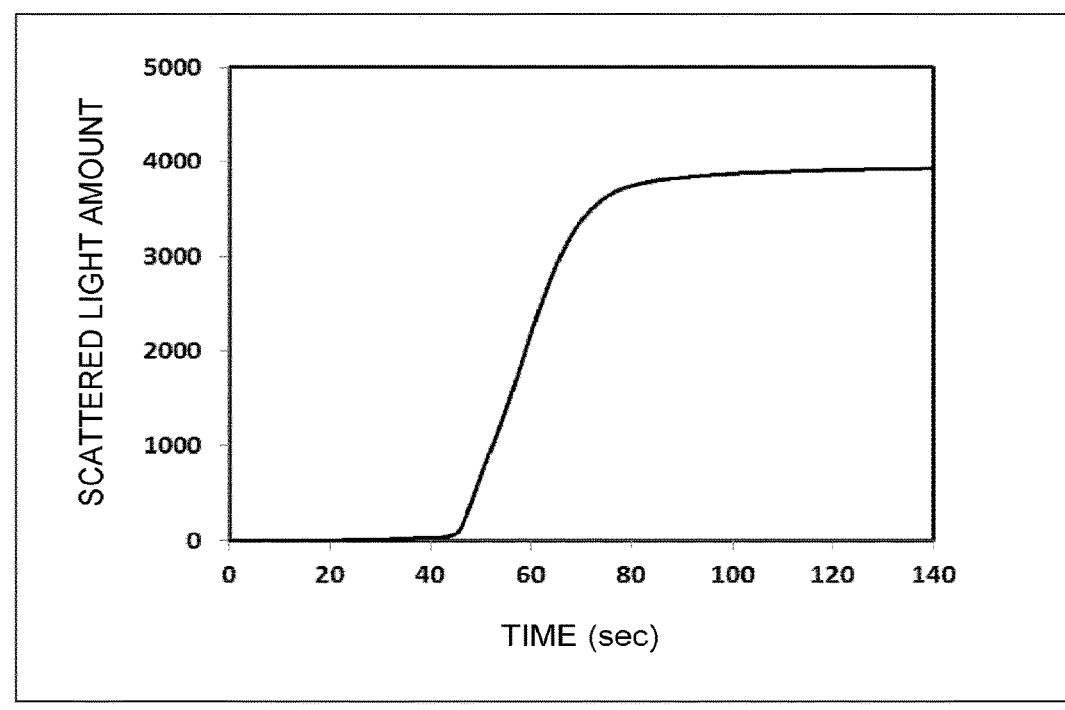
FIG. 4 is an example of a coagulation reaction curve after pre-processing.
Figure 5:
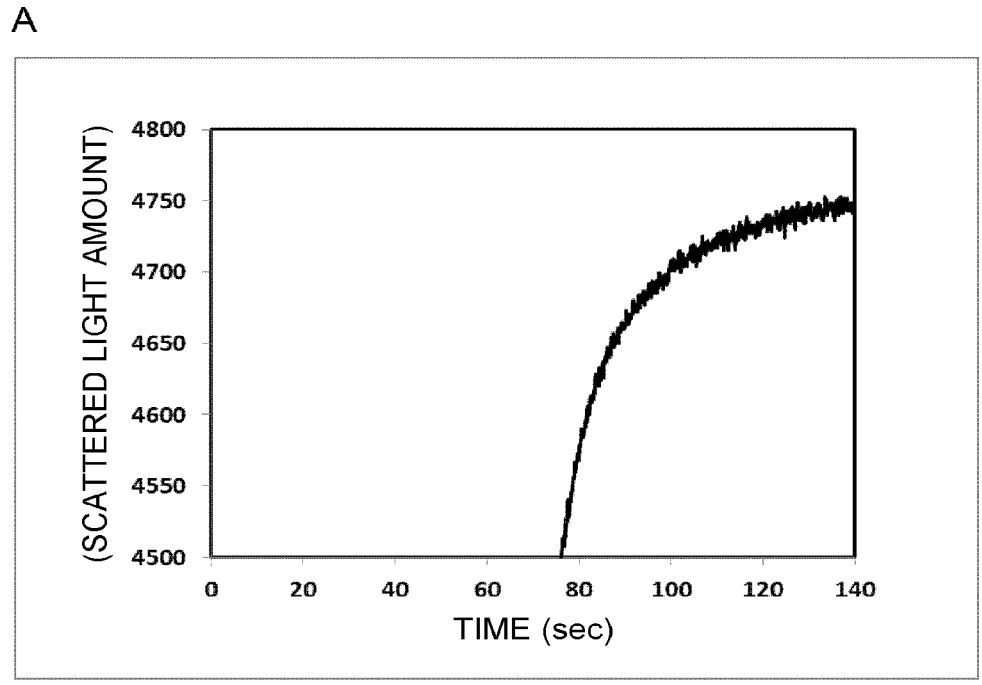
FIG. 5 shows A: a partially enlarged graph of an example of a coagulation reaction curve, and B: a partially enlarged graph of an example of a coagulation reaction curve after pre-processing.
Figure 5:
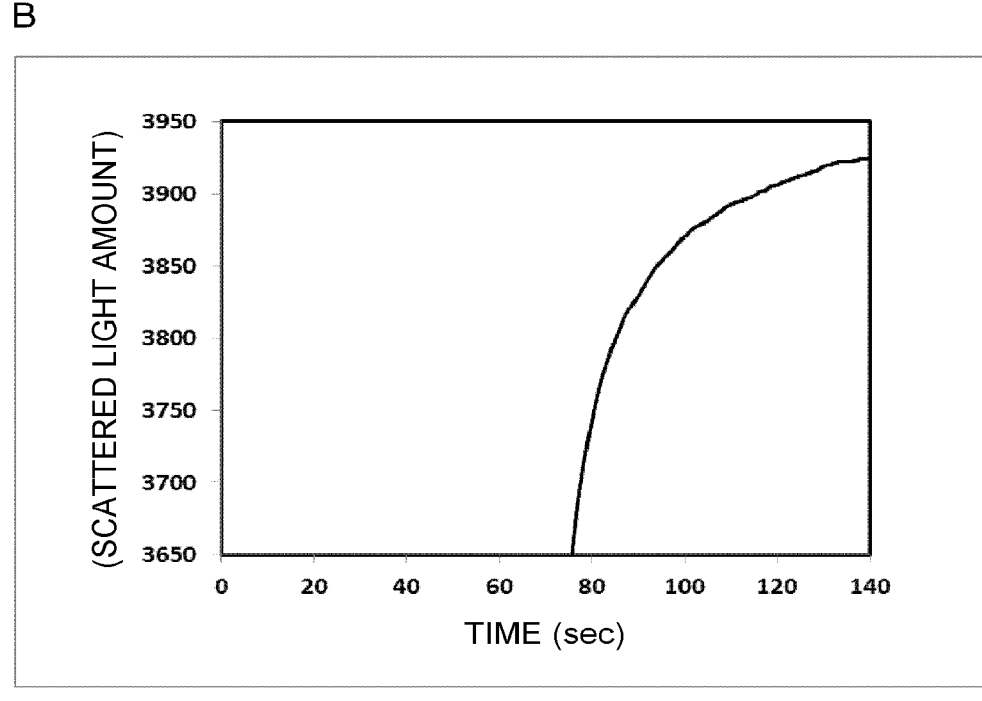

According to the need, the coagulation reaction curve may be subjected to pre-processing (step 2b). The pre-processing can include smoothing processing for removing noises or zero point adjustment. FIG. 4 shows an example of the coagulation reaction curve of FIG. 3 subjected to pre-processing (smoothing processing and zero point adjustment). As the smoothing processing, any of known noise-removing methods can be used. As shown in FIG. 3, since a mixed solution containing a subject specimen originally scatters light, the scattered light intensity at the point of time of starting measurement (time 0) is larger than 0. The scattered light intensity at time 0 is adjusted to 0 by zero point adjustment after smoothing processing, as shown in FIG. 4. A and B of FIG. 5 are partially enlarged graphs showing the coagulation reaction curve of FIG. 3 before and after pre-processing, respectively. In B of FIG. 5, smoothing processing and zero point adjustment are performed for the data of A of FIG. 5.

The height of a coagulation reaction curve depends on the fibrinogen concentration of a subject specimen. At the same time, since the fibrinogen concentration varies from individual to individual, the height of a coagulation reaction curve depends on the subject specimen. Accordingly, in the present method, according to the need, correction processing for converting the coagulation reaction curve after pre-processing to relative values is performed in step 2c. A coagulation reaction curve that does not depend on the fibrinogen concentration can be obtained by the correction processing, and thereby the difference in the shapes after pre-processing of the coagulation reaction curves of samples can be quantitatively compared to each other.

In an embodiment, the correction processing corrects a pre-processed coagulation reaction curve such that the maximum value becomes a prescribed value. Suitably, in the correction processing, corrected coagulation reaction curve P(t) is determined from a pre-processed coagulation reaction curve according to the following equation (1). In the equation (1), D(t) represents a coagulation reaction curve after pre-processing, Drange represents the width of change in D(t) (i.e., Dmax−Dmin), Dmax and Dmin represent the maximum value and minimum value, respectively, of D(t), and A is an arbitrary value representing the maximum value of the corrected coagulation reaction curve.

$$P(t)=[(D(t)-D\mathrm{min})/D\mathrm{range}]\times A \tag{1}$$

Figure 6:
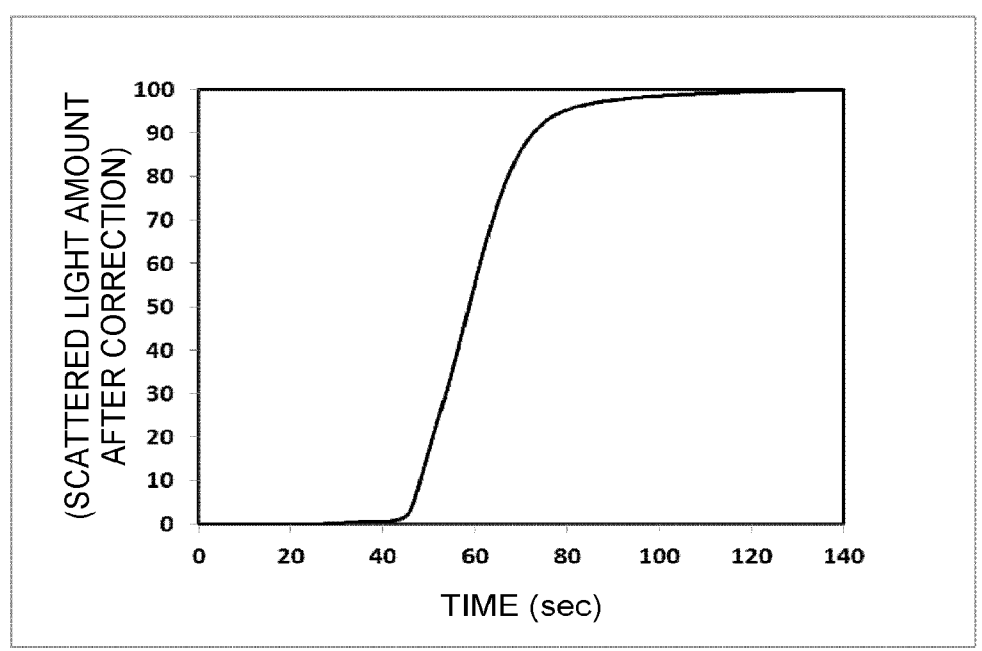
FIG. 6 is an example of a corrected zero-order curve.

As an example, FIG. 6 shows data corrected such that the maximum value of the coagulation reaction curve shown in FIG. 4 is 100. Although the correction in FIG. 6 has been performed such that the value after correction is from 0 to 100, other values (e.g., from 0 to 10,000, i.e., A=10,000 in the equation (1)) may be used. In addition, this correction processing does not necessarily have to be performed.

Alternatively, the correction processing described above may be performed for a waveform related to coagulation velocity described later or a parameter extracted from the waveform. For example, it is possible to calculate a waveform related to coagulation velocity of a pre-processed coagulation reaction curve D(t) that has not been subjected to correction processing and then convert the waveform to a value corresponding to P(t). Alternatively, it is possible to extract a parameter from the waveform related to coagulation velocity and then covert the value of the parameter to a value corresponding to P(t).

In the present specification, a corrected coagulation reaction curve as described above and a coagulation reaction curve not subjected to correction processing are also referred to as corrected zero-order curve and not-corrected zero-order curve, respectively, and they are also collectively referred to as "zero-order curves". In the present specification, the first-order differential curves of the corrected zero-order curve and the not-corrected zero-order curve are also referred to as corrected first-order curve and not-corrected first-order curve, and they are also collectively referred to as "first-order curves".

2.2) Calculation of Waveform Related to Coagulation Velocity

Figure 7:
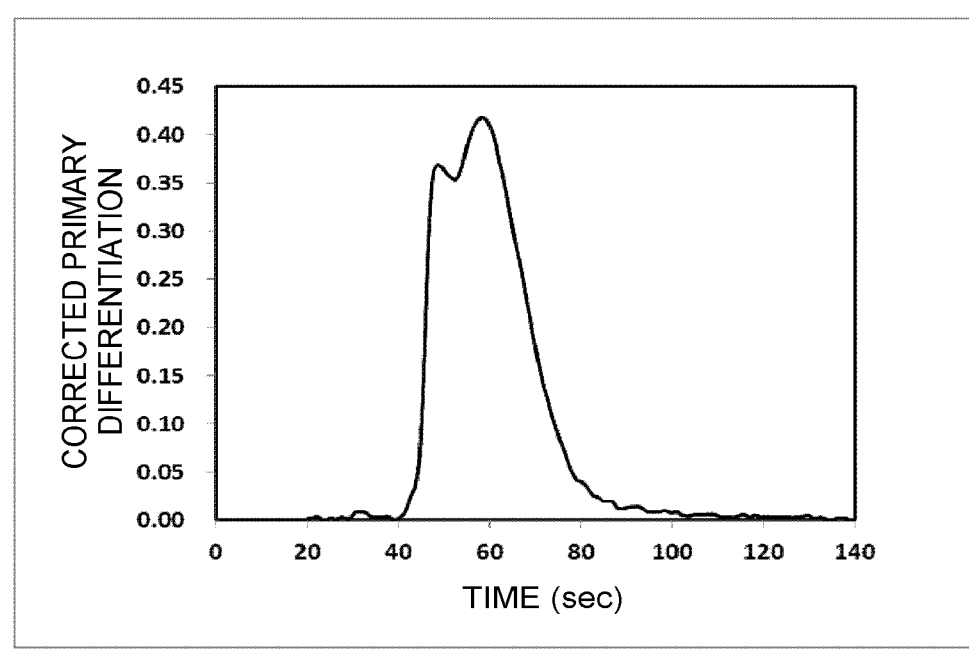
FIG. 7 is an example of a corrected first-order curve.

In step 2d, a waveform related to coagulation velocity is calculated. In the present specification, the waveform related to coagulation velocity includes a not-corrected first-order curve and a corrected first-order curve. The not-corrected first-order curve represents a value obtained by primary differentiation of a coagulation reaction curve (not-corrected zero-order curve), that is, a rate of change in the amount of coagulation reaction during arbitrary coagulation reaction time (coagulation velocity). The corrected first-order curve represents a value obtained by primary differentiation of a corrected coagulation reaction curve (corrected zero-order curve), that is, a relative rate of change in the amount of coagulation reaction during arbitrary coagulation reaction time. Accordingly, the waveform related to coagulation velocity can be a waveform representing coagulation velocity in the coagulation reaction of a sample or its relative value. In the present specification, values representing progress of blood coagulation including coagulation velocity represented by a first-order curve and its relative value may also be collectively referred to as primary differential values. Differentiation of a coagulation reaction curve or corrected coagulation reaction curve (not-corrected and corrected zero-order curves) can be performed using a known method. FIG. 7 shows a corrected first-order curve obtained by primary differentiation of the corrected zero-order curve shown in FIG. 6. The horizontal axis of FIG. 7 represents coagulation reaction time, and the vertical axis represents primary differentiation value.

2.3) Extraction of Parameter

In step 2e, a parameter characterizing the waveform related to coagulation velocity is extracted. In more detail, in the step of extracting the parameter, a prescribed calculation target area is extracted from the waveform related to coagulation velocity, and weighted average time of the calculation target area is then calculated. The blood coagulation time of a subject specimen can be determined based on the weighted average time (step 3). The parameter will be described below.

Figure 8:
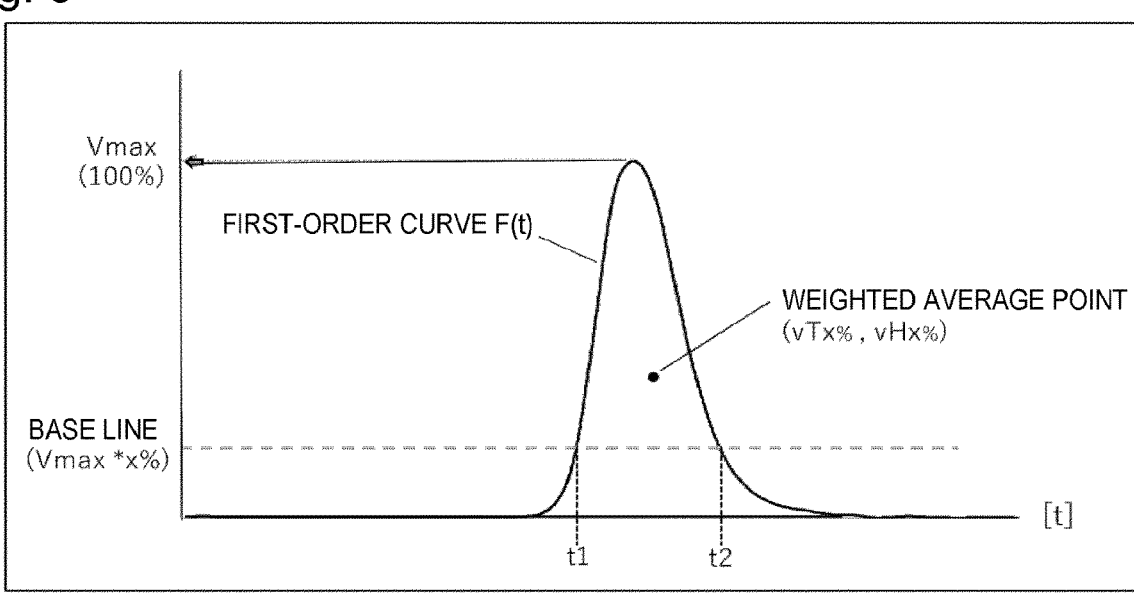
FIG. 8 is a conceptual graph showing a calculation target area and a weighted average point.

First, a process of extracting a predetermined calculation target area from a waveform related to coagulation velocity will be described. The calculation target area is a region on or above a predetermined lower limit value. In more detail, the calculation target area is a region (segment) where F(t) (t=time) denoting a waveform related to coagulation velocity (first-order curve) and Vmax denoting a maximum value of F(t) satisfy F(t)≥Vmax×x %. In more detail, the calculation target area is a region (segment) of a first-order curve F(t) satisfying Vmax≥F(t)≥ Vmax×x %. Accordingly, "Vmax×x %" represents the lower limit value of the calculation target area. The calculation target area will be described with reference to FIG. 8. FIG. 8 shows a first-order curve F(t) (t=time) and a maximum value Vmax of F(t). The base line indicating Vmax×x % is illustrated by a dotted line to indicate points of time t1 and t2 at which F(t)=Vmax×x %. The calculation target area is a region in which F(t) is equal to or higher than the base line and equal to or less than Vmax (F(t)≥Vmax×x %, t1≤t≤t2).

The weighted average point (vT, vH) corresponds to the "weighted average value" of a calculation target area. The coagulation reaction time (t) at a weighted average point is defined as weighted average time vT. That is, the weighted average time vT is time from the starting time of coagulation reaction until the weighted average point and is the x-coordinate of the weighted average point. The vT is the barycenter of the calculation target area for the horizontal axis direction. The weighted average height vH is the y-coordinate of the weighted average point.

In the present specification, a calculation target area based on a prescribed lower limit value and vT and vH derived from the calculation target area may be represented by the percentages with respect to Vmax of the lower limit value. For example, a calculation target area in which the lower limit value is x % of Vmax may be referred to as "x % calculation target area", and vT and vH derived from the "x % calculation target area" may be referred to as vTx % and vHx %, respectively. For example, a calculation target area in which the lower limit value is 20% of Vmax is referred to as 20% calculation target area, and the vT of the calculation target area is referred to as vT20%. FIG. 8 shows the weighted average point (vTx %, vHx %) of a calculation target area of F(t) with a lower limit value x %.

The weighted average time vT and weighted average height vH of a first-order curve can be determined by the following process. First, the maximum value of a first-order curve F(t) is defined as Vmax, the lower limit value of a calculation target area is defined as x % of the Vmax, and a data group of time t satisfying F(t)≥Vmax×x % is defined as t [t1, . . . , and t2] (t1<t2). That is, F (t1)=Vmax×x %, F (t2)=Vmax×x %, and the data group from time t1 to time t2 is t [t1, . . . , and t2] (t1<t2). On this occasion, the weighted average time vT and the weighted average height vH are calculated by the following equations (2) and (3), respectively. The weighted average point (vTx %, vHx %) of the x % calculation target area is induced from the determined vT and vH.

$$vT = \frac{\sum_{i=t1}^{t2}(i \times f(i))}{\sum_{i=t1}^{t2}F(i)} \tag{2}$$

$$vH = \frac{\sum_{i=t1}^{t2}(i \times f(i))}{\sum_{i=t1}^{t2}i} \tag{3}$$

The lower limit value of a calculation target area can be determined within a range of higher than 0% of Vmax and less than Vmax. The calculation target area reflects the shape of a first-order curve, and the larger the lower limit value, the upper part the calculation target area reflects the shape of the first-order curve. In the method of the present invention, the lower limit value ("Vmax×x %") of a calculation target area for calculating weighted average time to be used in measurement of coagulation time is preferably a prescribed value that is set in a range of 5% to 95% (i.e., x=5 to 95) of Vmax. In more detail, the lower limit value of a calculation target area for calculating weighted average time to be used for measurement of coagulation time is, when the coagulation time is APTT, a prescribed value set in a range of preferably 5% to 95% of Vmax (x=5 to 95), more preferably 5% to 50% of Vmax (x=5 to 50), and further preferably 10% to 35% of Vmax (x=10 to 35), and is, when the coagulation time is PT, a prescribed value set in a range of preferably 5% to 95% of Vmax (x=5 to 95), more preferably 10% to 80% of Vmax (x=10 to 80), and further preferably 25% to 50% of Vmax (x=25 to 50).

Figure 9:
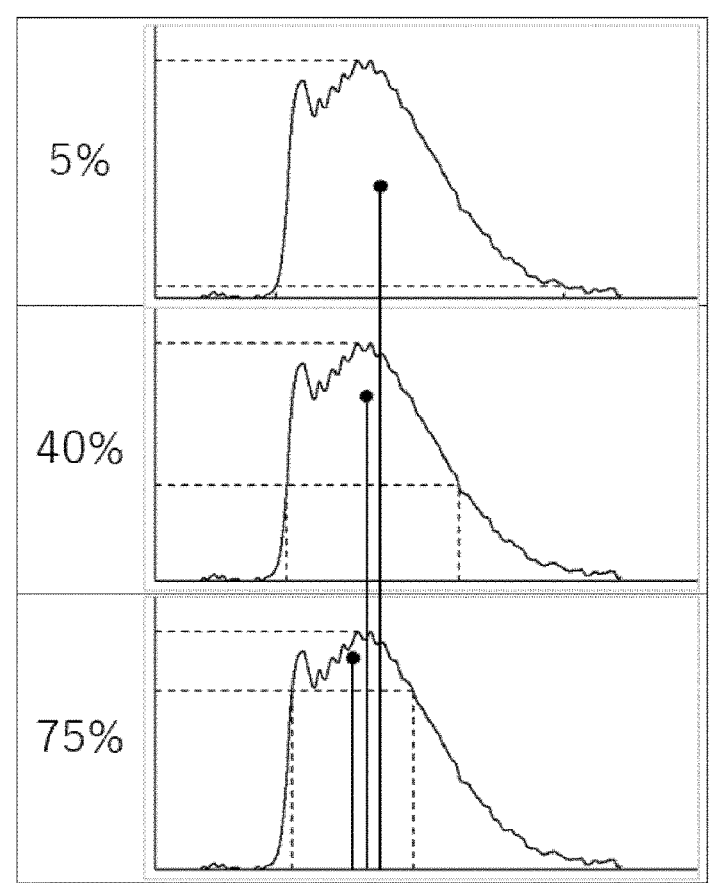
FIG. 9 is a conceptual graph showing a change in weighted average point depending on the calculation target area.

FIG. 9 shows a relationship between the calculation target area in a first-order curve and the calculated weighted average point. In FIG. 9, the upper, middle, and lower stages show the calculation target area and weighted average point (filled circled mark) of each of the first-order curves when the lower limit values are 5%, 40%, and 75%, respectively, of Vmax. The position of a weighted average point changes as the calculation target area changes, as shown in FIG. 9.

In FIGS. 8 and 9 above, a calculation target area and its weighted average point have been described as an example of a corrected first-order curve, but a similar parameter can be calculated also in a not-corrected first-order curve.

3. Coagulation Time Measurement

As shown in Examples below, the weighted average time vT calculated by the above-described process has a high correlation with the blood coagulation time of a subject specimen. Accordingly, it is possible to determine the coagulation time of a subject specimen based on the weighted average time vT. For example, when the coagulation time is APTT or PT, the weighted average time vT can be determined as coagulation time. In the method of the present invention, coagulation time measurement that is unlikely to be influenced by, for example, measurement noises and a bimodal peak caused by coagulation disorder, and has higher reliability, compared to the case of simply detecting the peak of a first-order curve, is possible by determining the weighted average of a first-order curve of coagulation reaction.

Furthermore, in the method of the present invention, coagulation time can be measured when the first-order curve of coagulation reaction arrives at maximum value Vmax and then reaches a lower limit value (Vmax×x %) or less of the calculation target area. Accordingly, in the method of the present invention, it is not necessary to continue the measurement until the coagulation reaction reaches the plateau, unlike the conventional percentage method. Furthermore, also when a large number of samples are analyzed by an automated analyzer, according to the method of the present invention, it is not necessary to set a long measurement time for an abnormal sample with low coagulability, unlike the conventional percentage method. Accordingly, according to the present invention, it is possible to reduce or optimize the analysis time of samples and thereby improve the analysis efficiency.

4. Measurement of Coagulation Factor Concentration

A normal blood includes coagulation factors, such as coagulation factors I to XIII, and abnormality and deficiency of these coagulation factors lead to abnormality of coagulability. Generally, the coagulation factor concentration of a subject specimen can be measured using a dedicated reagent for each coagulation factor based on the coagulation time of a measurement sample prepared from the subject specimen. Accordingly, the coagulation factor concentration of the subject specimen can be measured using the coagulation time of the measurement sample measured by the method of the present invention based on the weighted average time. Generally, the coagulation factor concentration is measured based on a standard curve showing a relationship between coagulation time and coagulation factor concentration. Accordingly, the coagulation factor concentration of the subject specimen can be measured by applying the coagulation time of the measurement sample measured by the method of the present invention to a standard curve made in advance. Preferable examples of the coagulation factor to be measured by the method of the present invention include factor I (fibrinogen), factor VIII, and factor IX.

In the method of the present invention, the lower limit value ("Vmax×x %") of a calculation target area for calculating the coagulation time (weighted average time) to be used in measurement of coagulation factor concentration is preferably a prescribed value set within a range of 5% to 95% (i.e., x=5 to 95) of Vmax, more preferably 30% to 95% (i.e., x=30 to 95) of Vmax, and further preferably 60% to 75% (i.e., x=60 to 75) of Vmax.

5. Application to Another Coagulation Reaction-Measuring Method

The method for measuring blood coagulation time of the present invention has been described above by the case of coagulation reaction measurement based on scattered light intensity as an example. However, the method of the present invention can be applied to a method for measuring blood coagulation time using another method for measuring coagulation reaction (for example, a method for measuring blood coagulation reaction based on transmittance, absorbance, viscosity, or the like) by those skilled in the art. For example, the positive and negative of a first-order curve F(t) obtained from an inverse sigmoid-like coagulation reaction curve based on the amount of transmitted light or the like become reversed with respect to those based on the amount of scattered light described above. It is obvious to those skilled in the art that in such a case, the sign of F(t) in the calculation of a parameter is reversed, for example, the maximum value Vmax is substituted by the minimum value Vmin, and the x % calculation target area is a region satisfying $F(t) \leq Vmin \times x$ %.

EXAMPLES

The present invention will now be described in further detail with examples, but is not limited to these examples.

Example 1: Measurement of Coagulation Time (APTT) Based on Weighted Average Time 1. Method 1.1) Sample As subject specimens, 9 normal plasma samples and 15 abnormal plasma samples with elongated APTT, 24 samples in total, were used. As the normal plasma, Normal Donor Plasma manufactured by CliniSys Associates, Ltd. was used. In the abnormal plasma, as coagulation factor deficiency plasma (factor deficient plasma), 2 samples each of factor FVIII deficiency plasma, factor FIX deficiency plasma, factor FXI deficiency plasma, and factor FXII deficiency plasma, 2 samples of lupus anticoagulant positive plasma (Lupus Anticoagulant Plasma), and 5 samples of unfractionated heparin-containing plasma (Anticoagulant Plasma) (all of them are manufactured by CliniSys Associates, Ltd.) were used.

1.2) Reagent

As the APTT reagent, Coagpia APTT-N (manufactured by Sekisui Medical Co., Ltd.) was used.

1.3) Coagulation Reaction Measurement

Coagulation reaction measurement was performed using an automated blood coagulation analyzer CP3000 (manufactured by Sekisui Medical Co., Ltd.). Each (50 µL) of the samples was dispensed in a cuvette (reaction container) and was then warmed at 37° C. for 45 seconds, the APTT reagent (50 µL) warmed to about 37° C. was then added to the cuvette, and, after 171 seconds, a calcium chloride solution (50 µL) was further added thereto to start coagulation reaction. The reaction was performed while keeping the temperature about 37° C. The measurement (photometry) of coagulation reaction was performed by irradiating the cuvette with light having a wavelength of 660 nm from an LED light as a light source and measuring the amount of 90-degree side scattered light at 0.1 seconds intervals. The maximum measurement time was 360 seconds (number of data: 3600, 0.1 seconds intervals).

1.4) APTT Measurement (Percentage Method)

The APTT of each sample was measured by a percentage method. That is, the point of time at which the amount of scattered light arrived at the maximum value within the measurement time was determined as the coagulation reaction end point, and the point of time at which the amount of scattered light reached 50% of the coagulation reaction end point was determined as APTT. Table 1 shows the category and number of subject specimens and the minimum and maximum values of APTT in the samples of each category.

TABLE 1

| Sample category | Number of samples | APTT (sec) Minimum value | APTT (sec) Maximum value |
|---|---|---|---|
| Normal plasma | 9 | 27.2 | 35.4 |
| FVIII deficient plasma | 2 | 38.3 | 141.2 |
| FIX deficient plasma | 2 | 34.2 | 75.1 |
| FXI deficient plasma | 2 | 42.3 | 87.6 |
| FXII deficient plasma | 2 | 35.1 | 81.0 |
| LA positive plasma | 2 | 55.0 | 78.4 |
| Heparin-containing plasma | 5 | 38.2 | 126.2 |

1.5) Production of Coagulation Reaction Curve

A coagulation reaction curve P(t) was calculated by subjecting the photometric data from each sample to smoothing processing including noise removal and then performing zero point adjustment processing such that the scattered light intensity at the point of time of starting photometry is 0. Subsequently, a corrected first-order curve was calculated by performing correction such that the maximum value Pmax of the coagulation reaction curve is 100 and performing primary differentiation of the resulting corrected coagulation reaction curve (corrected zero-order curve).

1.6) Calculation of Weighted Average Time vT

Weighted average time (vT5% to vT95%) of each of 5% to 95% calculation target areas was calculated from the first-order curve obtained from each sample. The lower limit value x % of a calculation target area was set to 19 levels of 58, 108, 158, 208, 258, 308, 358, 408, 458, 508, 55%, 608, 658, 70%, 758, 80%, 858, 90%, and 95% of the maximum height Vmax (100%) of the first-order curve F(t), and time t1 and time t2 (t1<t2) each satisfying F(t)=Vmaxxx % were determined. Using the equation (2) above, 19 weighted average time vT5% to vT95% were calculated for each of 24 samples.

2. APTT Measurement Based on Weighted Average Time 2.1) Correlation Between Weighted Average Time and APTT The correlation between APTT by a percentage method and weighted average time was evaluated. Primary regression analysis of weighted average time (vT5% to vT95%) of 5% to 95% calculation target areas with APTT by a percentage method was performed, and the slope, intercept, and correlation coefficient of each regression line were determined.

Figure 10:
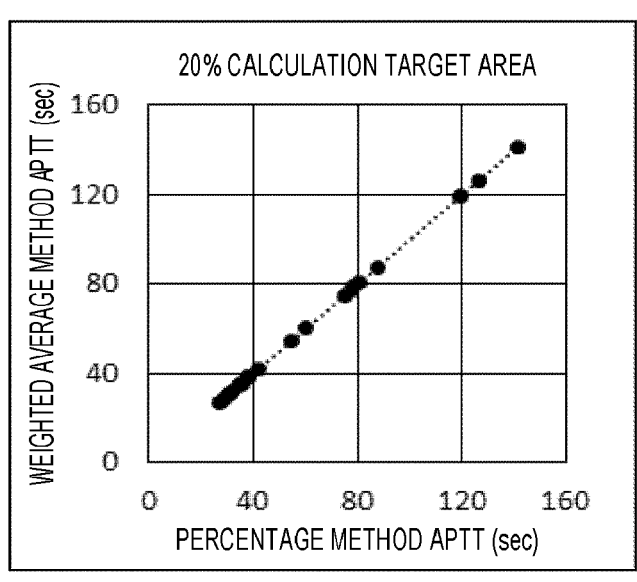
FIG. 10 is a primary regression line of vT20% in a 20% calculation target area with respect to APTT by a percentage method.
Figure 11:
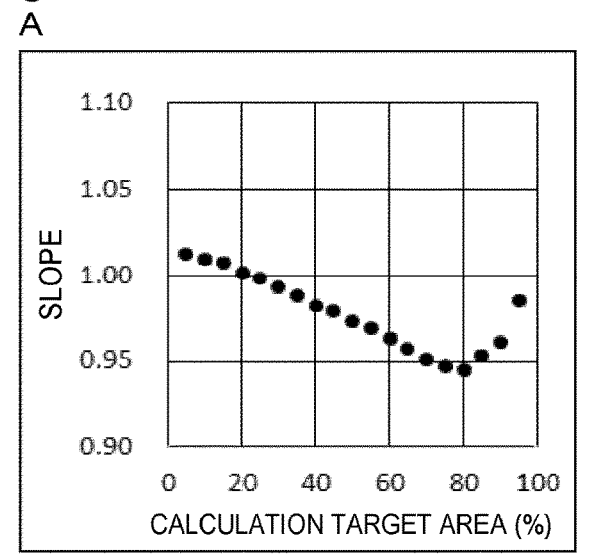
FIG. 11 shows the slopes (A), intercepts (B), and correlation coefficients (C) of primary regression lines of vT (vT5% to vT95%) in 5% to 95% calculation target areas with respect to APTT by a percentage method.
Figure 11:
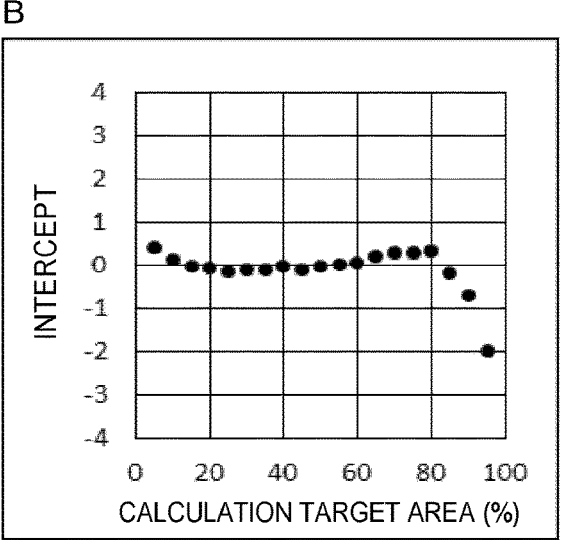
Figure 11:
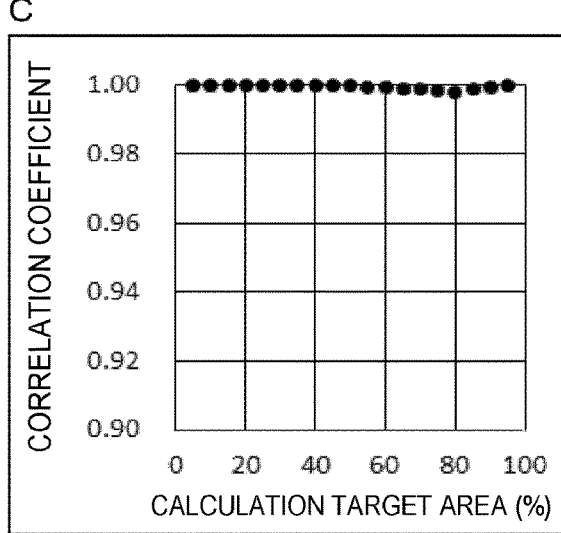

FIG. 10 shows a primary regression line of vT20% in a 20% calculation target area with respect to APTT by a percentage method for 24 samples. vT20% had a high correlation with APTT by a percentage method. FIG. 11 shows the slopes, intercepts, and correlation coefficients of the primary regression lines of vT (vT5% to vT95%) in 5% to 95% calculation target areas with respect to APTT by a percentage method. In the 5% to 95% calculation target areas, the slopes of the regression lines were 0.95 to 1.01, the intercepts were −2.0 to 0.4, and the correlation coefficients were 0.998 to 1.000 (A to C of FIG. 11). It was confirmed that the APTT measuring method based on weighted average time has performance satisfying In-vitro diagnostic drug approval criteria, "comparing to control measurement method, the correlation coefficient is 0.9 or more, and the slope of regression line equation is 0.9 to 1.1", by the Ministry of Health, Labour and Welfare, in all conditions of the calculation target areas from 5% to 95%. It was revealed from these results that APTT can be measured based on vT.

2.2) Accuracy of Measurement

The weighted average time in each of 5% to 95% calculation target areas of 24 samples was compared to a control (APTT by a percentage method). Each row of the tables A and B of FIG. 12 represents weighted average time (vT5% to vT95%) of each sample. When the difference between weighted average time and the control is within ±5% (A of FIG. 12) or within ±2.58 (B of FIG. 12) of the control, it is represented by gray color. In the 5% to 50% calculation target areas, the weighted average time of all samples agreed with the control within an error of ±5%, and in the 10% to 35% calculation target areas, the weighted average time of all samples agreed with the control within an error of ±2.5%.

Example 2: Coagulation Time (PT) Measurement Based on Weighted Average Time

1. Method 1.1) Sample

As subject specimens, nine normal plasma samples and 14 abnormal plasma samples with elongated PT, 23 samples in total, were used. As the normal plasma, plasma of normal subjects was used. As the abnormal plasma, plasma of patients administered with warfarin as an anticoagulant and having a PT-INR value, which indicates blood warfarin concentration, of 1 to 2 (five samples), of 2 to 3 (five samples), and of 3 to 4 (four samples) was used.

1.2) Coagulation Reaction Measurement

The coagulation reaction measurement was performed using an automated blood coagulation analyzer CP3000 (manufactured by Sekisui Medical Co., Ltd.). Each (50 µL) of the samples was dispensed in a cuvette (reaction container) and was then warmed at 37° C. for 45 seconds, and a thromboplastin solution (100 µL) warmed to about 37° C. was then added to the cuvette to start coagulation reaction. The reaction was performed while keeping the temperature about 37° C. The measurement (photometry) of coagulation reaction was performed by irradiating the cuvette with light having a wavelength of 660 nm from an LED light as a light source and measuring the amount of 90-degree side scattered light at 0.1 seconds intervals. The maximum measurement time was 300 seconds (number of data: 3000, 0.1 seconds intervals).

1.3) PT Measurement (Percentage Method)

The PT of each sample was measured by a percentage method. The point of time at which the amount of scattered light arrived at the maximum value within the measurement time was determined as the coagulation reaction end point, and the point of time at which the amount of scattered light arrived at 45% of the coagulation reaction end point was determined as PT. Table 2 shows the category and number of subject specimens and the minimum and maximum values of PT in the samples of each category.

TABLE 2

| Sample category | Number of samples | PT (sec) Minimum value | PT (sec) Maximum value |
|---|---|---|---|
| Normal plasma | 9 | 11.4 | 12.1 |
| PT-INR 1-2 | 5 | 9.5 | 23.4 |
| PT-INR 2-3 | 5 | 20.6 | 28.6 |
| PT-INR 3-4 | 4 | 31.3 | 51.6 |

1.4) Calculation of Weighted Average Time vT

The corrected first-order curves of 23 samples were calculated by the same process as in 1.5) and 1.6) of Example 1, and weighted average time vT5% to vT95% were calculated.

2. PT Measurement Based on Weighted Average Time 2.1) Correlation Between Weighted Average Time and PT By the same process as in 2.1) of Example 1, primary regression analysis of weighted average time (vT5% to vT95%) of 5% to 95% calculation target areas with PT by a percentage method was performed and the slope, intercept, and correlation coefficient of each regression line were determined.

Figure 13:
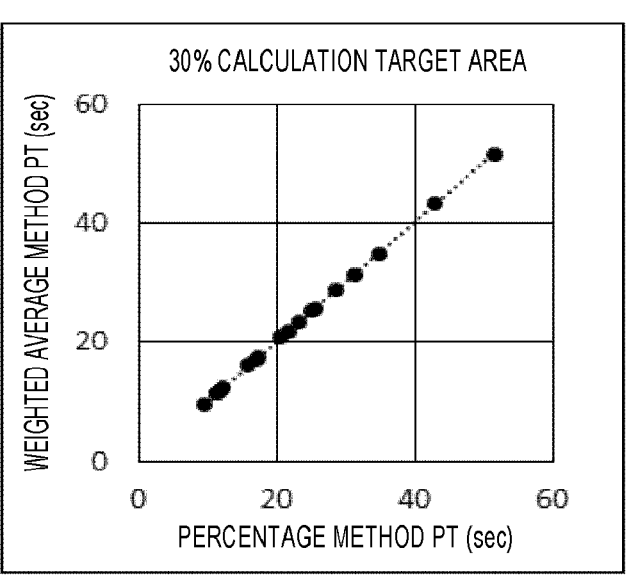
FIG. 13 is a primary regression line of vT30% in a 30% calculation target area with respect to PT by a percentage method.
Figure 14:
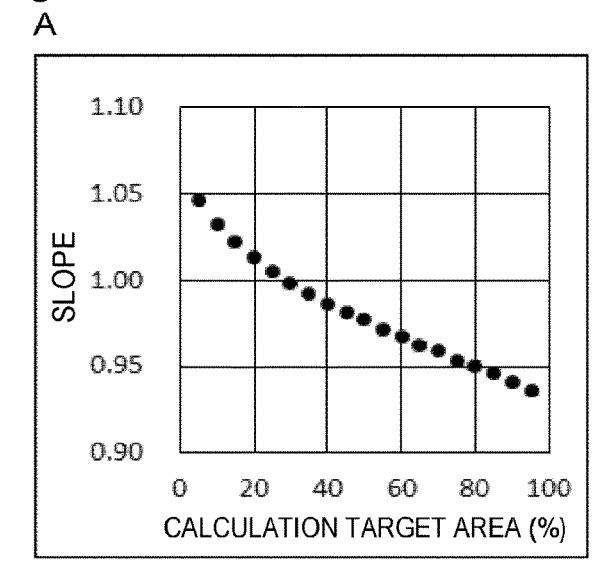
FIG. 14 shows the slopes (A), intercepts (B), and correlation coefficients (C) of primary regression lines of vT (vT5% to vT95%) in 5% to 95% calculation target areas with respect to PT by a percentage method.
Figure 14:
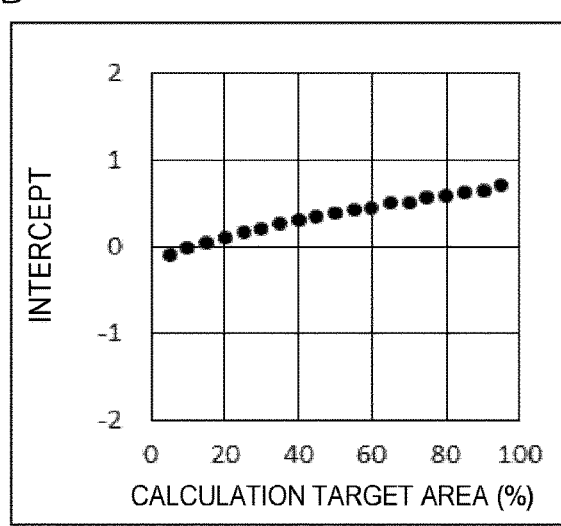
Figure 14:
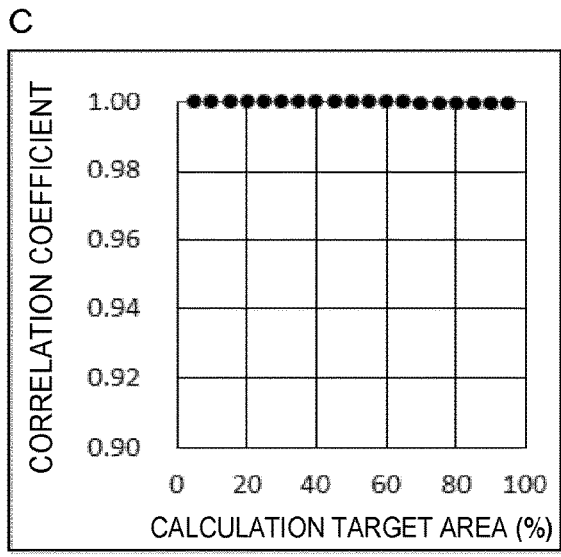

FIG. 13 shows a primary regression line of vT30% in a 30% calculation target area with respect to PT by a percentage method for 23 samples. vT30% had a high correlation with PT by a percentage method. FIG. 14 shows the slopes, intercepts, and correlation coefficients of the primary regression lines of vT (vT5% to vT95%) in 5% to 95% calculation target areas with respect to PT by a percentage method. In the 5% to 95% calculation target areas, the slopes of the regression lines were 0.94 to 1.05, the intercepts were –1.0 to 0.7, and the correlation coefficients were all 1.000 (A to C of FIG. 14). It was confirmed that the PT measuring method based on weighted average time has performance satisfying In-vitro diagnostic drug approval criteria, "comparing to control measurement method, the correlation coefficient is 0.9 or more, and the slope of regression line equation is 0.9 to 1.1", by the Ministry of Health, Labour and Welfare, in all conditions of the calculation target areas from 5% to 95%. It was revealed from these results that PT can be measured based on vT.

2.2) Accuracy of Measurement

The weighted average time in each of 5% to 95% calculation target areas of 23 samples was compared to a control (PT by a percentage method). Each row of the tables of A and B of FIG. 15 represents weighted average time (vT5% to vT95%) of each sample. When the difference between weighted average time and the control is within ±5% (A of FIG. 15) or within ±2.5% (B of FIG. 15) of the control, it is represented by gray color. In the 10% to 80% calculation target areas, the weighted average time of all samples agreed with the control within an error of ±58, and in the 25% to 50% calculation target areas, the weighted average time of all samples agreed with the control within an error of ±2.5%.

Example 3: Fibrinogen Concentration Measurement Based on Weighted Average Time

1. Method 1.1) Sample

Human fibrinogen (Human Fibrinogen manufactured by Enzyme Research Laboratories, Product name: FIB 2) was added to human fibrinogen-removed plasma (Fibrinogen Deficient Human Plasma manufactured by Affinity Biologicals Inc., Product name: Fg Deficient Plasma) to produce a sample (sample 10) with a fibrinogen concentration ([Fbg]) of 980 mg/dL. As standard samples for producing a standard curve, the sample 10 and a physiological saline solution were mixed at volume ratios of 1:9, 7:3, and 10:0 to prepare three samples with fibrinogen concentration ([Fbg]) of 98 mg/dL, 686 mg/dL, and 980 mg/dL, respectively. Separately, the sample 10 and the human fibrinogen-removed plasma were mixed at volume ratios of 1:9 to 10:0 to prepare ten concentration series samples with stepwise different fibrinogen concentrations ([Fbg]) (Table 3).

TABLE 3

| Sample | Dilution ratio | [Fbg] (mg/dl) |
|---|---|---|
| 1 | 1:9 | 98 |
| 2 | 2:8 | 196 |
| 3 | 3:7 | 294 |
| 4 | 4:6 | 392 |
| 5 | 5:5 | 490 |
| 6 | 6:4 | 588 |
| 7 | 7:3 | 686 |
| 8 | 8:2 | 784 |

TABLE 3-continued

| Sample | Dilution ratio | [Fbg] (mg/dl) |
|---|---|---|
| 9 | 9:1 | 882 |
| 10 | 10:0 | 980 |

1.2) Coagulation Reaction Measurement

As the fibrinogen measurement reagents, the thrombin reagent and sample diluent included in Coagpia Fbg (manufactured by Sekisui Medical Co., Ltd.) were used. The coagulation reaction measurement was performed using an automated blood coagulation analyzer CP3000 (manufactured by Sekisui Medical Co., Ltd.). A sample (10 μL) and the sample diluent (90 μL) were dispensed in a cuvette and were warmed at 37° C. for 45 seconds, and a thrombin reagent (50 μL) warmed to about 37° C. was then added to the cuvette to start coagulation reaction. The reaction was performed while keeping the temperature about 37° C. The coagulation reaction measurement was performed by irradiating the cuvette with light having a wavelength of 660 nm from an LED light as a light source and measuring the amount of 90-degree side scattered light at 0.1 seconds intervals. The maximum measurement time was 300 seconds (number of data: 3000, 0.1 seconds intervals). The measurement of coagulation reaction was performed twice for each of three standard samples and ten concentration series samples.

1.3) Calculation of Fibrinogen Concentration by Coagulation Time Measurement (Percentage Method)

Coagulation times of three standard samples and ten concentration series samples were measured by a percentage method. That is, the point of time at which the amount of scattered light arrived at 63% of the coagulation reaction end point was determined as the coagulation time. The coagulation time of each sample was measured twice based on the coagulation reaction measurement each performed twice. Regarding the coagulation times measured twice for each of the three standard samples, averages of the duplicate measurements were calculated, and logarithms of the averages were plotted with respect to the logarithms of [Fbg] (mg/dL) of the standard samples to produce a standard curve by a percentage method. According to the produced standard curve, the fibrinogen concentration ([Fbg] arithmetic value by a percentage method, mg/dL) of each of the concentration series samples was calculated.

1.4) Calculation of Fibrinogen Concentration by Weighted Average Time vT

Weighted average time vT5% to vT95% of ten concentration series samples were calculated twice for each by the same process as in 1.5) and 1.6) of Example 1 to obtain data of the weighted average time for 20 samples. In addition, weighted average time vT5% to vT95% of the three standard samples were calculated twice for each, and averages of the duplicate measurements were calculated. Logarithms of the averages were plotted with respect to the logarithms of [Fbg] (mg/dL) of the standard samples to produce a standard curve by weighted average time. According to the produced standard curve, the fibrinogen concentration ([Fbg] arithmetic value by weighted average time, mg/dL) of each of the concentration series samples was calculated.

Figure 16:
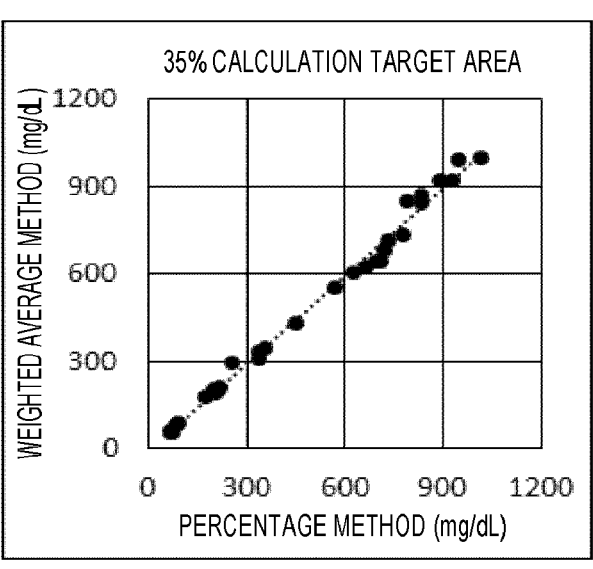
FIG. 16 shows a primary regression line of [Fbg] arithmetic value by weighted average time in a 35% calculation target area with respect of [Fbg] arithmetic value by a percentage method.
Figure 17:
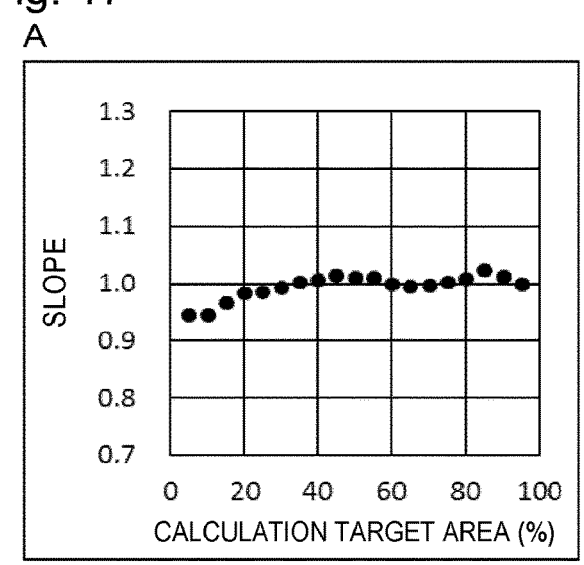
FIG. 17 shows the slopes (A), intercepts (B), and correlation coefficients (C) of primary regression lines of [Fbg] arithmetic values based on vT (vT5% to vT95%) in 5% to 95% calculation target areas with respect to [Fbg] arithmetic values by a percentage method.
Figure 17:
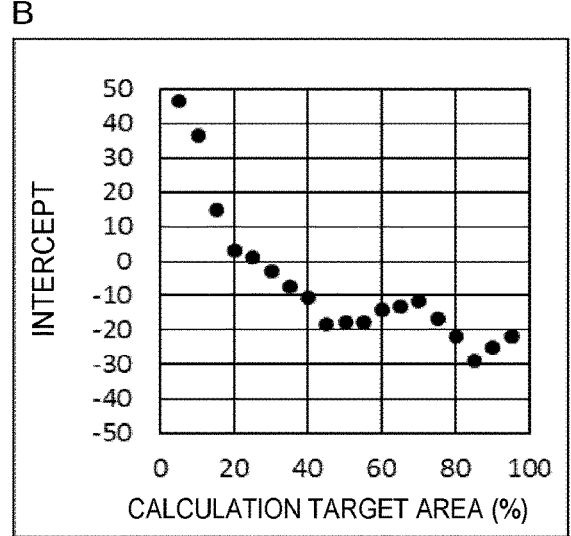
Figure 17:
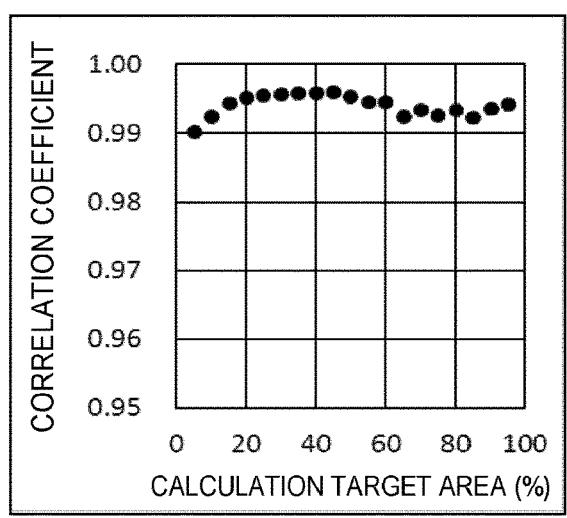

2. Evaluation of Fibrinogen Concentration Measurement Based on Weighted Average Time 2.1) Correlation Analysis FIG. 16 shows a primary regression line of [Fbg] arithmetic value (mg/dL) by weighted average time calculated from vT35% in a 35% calculation target area with respect of [Fbg] arithmetic value by a percentage method based on concentration series sample data (n=10×2). The [Fbg] arithmetic value based on vT35% had a high correlation with the [Fbg] arithmetic value by a percentage method. FIG. 17 shows the slopes, intercepts, and correlation coefficients of the primary regression lines of [Fbg] arithmetic values calculated from vT (vT5% to vT95%) in 5% to 95% calculation target areas with respect to [Fbg] arithmetic value by a percentage method. In the 5% to 95% calculation target areas, the slopes of the regression lines were 0.94 to 1.02, the intercepts were −31.5 to 51.0, and the correlation coefficients were 0.990 to 0.996 (A to C of FIG. 17). It was confirmed that the fibrinogen concentration measuring method based on weighted average time leads to the results similar to those of a standard method based on a percentage method in all conditions of the calculation target areas from 5% to 95%, and accordingly has performance satisfying In-vitro diagnostic drug approval criteria, "comparing to control measurement method, the correlation coefficient is 0.9 or more, and the slope of regression line equation is 0.9 to 1.1", by the Ministry of Health, Labour and Welfare. It was revealed from these results that fibrinogen concentration can be measured based on vT.

2.2) Accuracy of Measurement

[Fbg] arithmetic values of concentration series sample data (10 samples of Table 3×2) based on weighted average time in 5% to 95% calculation target areas were compared to expected values (Fbg concentrations of samples shown in Table 3). Each row of the tables A and B of FIG. 18 represents weighted average time (vT5% to vT95%) of each sample. When the error between [Fbg] arithmetic value based on weighted average time and the expected value is within ±10% (A of FIG. 18) or within ±5% (B of FIG. 18), it is represented by gray color. In 30% to 95% calculation target areas, the errors of [Fbg] arithmetic values of all samples were within ±10, and in 60% to 75% calculation target areas, the errors of [Fbg] arithmetic values of all samples were within ±5.

The invention claimed is:

1. A method for measuring blood coagulation time, comprising:
  measuring coagulation reaction of a sample prepared by mixing a subject blood specimen and a coagulation time measurement reagent to obtain measurement data;
  calculating weighted average time of a first order differential curve of a coagulation reaction curve from the obtained measurement data; and
  determining the weighted average time as blood coagulation time of the subject blood specimen, wherein
  the weighted average time is represented by a following equation, where F(t), wherein t is time, is the first-order differential curve of the coagulation reaction curve, and t1 and t2, wherein t1<t2, are times when F(t) is x %, wherein x is a prescribed value set within a range of 5 to 95, of the maximum value of F(t):

$$\text{Weighted average time} = \frac{\sum_{i=t1}^{t2}(i \times F(i))}{\sum_{i=t1}^{t2}F(i)}.$$

2. The method according to claim 1, wherein the subject blood specimen is plasma.

3. The method according to claim 1, wherein the blood coagulation time is activated partial thromboplastin time (APTT), prothrombin time (PT), or coagulation time by fibrinogen concentration measurement.

4. A method for measuring coagulation factor concentration, comprising measuring coagulation factor concentration of a subject blood specimen based on blood coagulation time of the subject blood specimen measured by the method according to claim 1, wherein the coagulation factor concentration is measured based on a standard curve showing a relationship between the blood coagulation time and the coagulation factor concentration.

5. The method according to claim 4, wherein the subject blood specimen is plasma.

6. The method according to claim 4, wherein the coagulation factor is fibrinogen.

7. The method according to claim 6, wherein the blood coagulation time is coagulation time by fibrinogen concentration measurement.

* * * * *